United States Patent [19]

Kurono et al.

[11] Patent Number: 5,356,880

[45] Date of Patent: Oct. 18, 1994

[54] GLYCYRRHETINIC ACID DERIVATIVES

[75] Inventors: Masayasu Kurono; Yoshiro Ishiwata; Syoji Yokochi; Kyoichi Asano; Takahiko Mitani; Takuji Kakigami; Noriyuki Iwata; Kougaku Isogawa; Yutaka Baba; Hiroyuki Ohwaki; Kiichi Sawai; Hiromoto Kimura; Masato Fukushima; Ryoichi Unno; Tamaki Ohtuka, all of Nagoya, Japan

[73] Assignee: Sanwa Kagaku Kenkyusho Co., Ltd., Nagoya, Japan

[21] Appl. No.: 889,709

[22] Filed: May 28, 1992

[30] Foreign Application Priority Data

May 30, 1991 [JP] Japan .................................. 3-127271
Mar. 12, 1992 [JP] Japan .................................. 4-053929

[51] Int. Cl.$^5$ .................. A61K 31/58; C07J 43/00
[52] U.S. Cl. .................................. 514/26; 536/5
[58] Field of Search ................ 514/23, 25, 26, 53, 514/54, 61, 176, 179, 247, 319, 638, 656; 536/4.1, 5, 17.2, 17.3, 17.4, 17.9, 115, 18.4; 540/15, 47, 107

[56] References Cited

U.S. PATENT DOCUMENTS

| | | | |
|---|---|---|---|
| 4,879,376 | 11/1989 | Foresta et al. | 536/5 |
| 4,918,171 | 4/1990 | Oshio et al. | 536/5 |
| 5,019,495 | 5/1991 | Shanbrom | 435/1 |
| 5,128,149 | 7/1992 | Shanbrom | 424/529 |
| 5,128,150 | 7/1992 | Shanbrom | 424/533 |
| 5,147,859 | 9/1992 | Bombardelli et al. | 536/5 |

FOREIGN PATENT DOCUMENTS

| | | |
|---|---|---|
| 1396317 | 7/1990 | European Pat. Off. |
| 1271081 | 9/1977 | Fed. Rep. of Germany |
| 63-243093 | 1/1989 | Japan |
| 63-135351 | 10/1989 | Japan |
| 1567307 | 5/1980 | United Kingdom ............ 536/5 |
| 2122893 | 1/1984 | United Kingdom |

OTHER PUBLICATIONS

Chemical Abstracts; vol. 113; Jul. 9, 1990; No. 2, Abstract No. 12139s.
Patent Abstract of Japan; 63-243093(A); vol. 13; No. 42 (C0565)(3390) Jan. 30, 1989. Isowa JP63-243093.
Patent Abstract of Japan; vol. 12; No. 387(C-536)(3234) Oct. 14, 1988. Kurono JP63-135351.
Hirabayashi et al.; *Chemical and Pharmaceutical Bulletin*, vol. 39(1), pp. 112–115, (1991).
Vanstone et al.; Chemical Abstracts 103:71555r (1985).
Dargan et al.; J. Gen. Virol. 67:1831–1850 (1986).
Vanstone et al.; Chemical Abstracts 106:18882f (1987).
Ito et al.; Antiviral Research 10:289–298 (Dec. 11, 1988).
Crance et al.; Journal of Medical Virology 31:155–160 (Jun. 1990).
Dargan et al.; Journal of General Virology 73:407–411 (Feb. 1992).
Garcia-Villalon et al.; Chemical Abstracts 117:316s (Jul. 6, 1992).
Sakai et al.; Chemical and Pharmaceutical Bulletin 38(3):824–826 (1990).

*Primary Examiner*—Johnnie R. Brown
*Assistant Examiner*—Howard C. Lee
*Attorney, Agent, or Firm*—Armstrong, Westerman, Hattori, McLeland & Naughton

[57] ABSTRACT

The invention provides a novel glycoside which contains as the aglycon a 4-(substituted phenyl)piperazine-1-yl derivative of glycyrrhetinic acid and 11-deoxoglycyrrhetinic acid or their derivative as well as a composition for the treatment of virus infection, which contains these compounds as a main active component.

7 Claims, No Drawings

GLYCYRRHETINIC ACID DERIVATIVES

BACKGROUND OF THE INVENTION

1. Field of the Invention

The present invention relates to novel glycyrrhetinic acid derivatives which can be used as the main active components of medicaments for the treatment of virus infections.

2. Description of the Prior Art

Glycyrrhetinic acid and certain of its derivatives are known to have anti-ulcer, anti-inflammatory, antiallergic, anti-hepatitis and antiviral activity. Among such compounds known so far in the art, for instance, there are carbenoxolone (U.S. Pat. No. 3,070,623), glycyrrhetinic acid ester derivatives having substituents at the 30-position (U.S. Pat. No. 3,070,624), amino acid salts of glycyrrhetinic acid (Japanese Patent Publication No. 44-32798), amide derivatives of glycyrrhetinic acid (Belgian Patent No. 753773), amide derivatives of 11-deoxoglycyrrhetinic acid (British Patent No. 1346871), cicloxolone ("Journal of Antimicrobial Chemotherapy", Vol 18, Suppl. B, pp. 185-200 (1986)), and glycyrrhizic acid and its derivatives ("Chem. Pharm. Bull.", 39(1), pp. 112-115 (1991)). Apart from these, we have also come up with a novel method of synthesizing 11-deoxoglycyrrhetinic acid (Japanese Patent Laid-Open Publication No. 59-70638) as well as its hemi-ester derivatives (Japanese Patent Laid-Open Publication No. 58-8044) and its carboxylic acid and amide derivatives (Japanese Patent Laid-Open Publication No. 63-135351).

As already noted, glycyrrhetinic acid and its derivatives have a variety of useful pharmacological activities. Never until now, however, has there been any report that they have sufficient antiviral for therapeutic use. In addition, they have some serious drawbacks, e.g., they show cytotoxicity in tests where they are used at concentrations high enough to achieve antiviral activity, they are unstable in aqueous solutions, and so on.

In recent years, other antiviral agents, based on acyclovir, based on a nucleic acid have been developed and found to be clinically efficacious against herpes virus infections in particular. However, another problem has arisen in connection with resistant viruses (e.g., thymidine kinase negative one) infections ("Oral. Surg. Oral. Med. Oral. Pathol", Vol. 67, pp. 427-432 (1989)). These nucleic acid type antiviral drugs have also generally been known to be ineffective against RNA virses such as influenza virus. In addition, it has been pointed out that they have some therapeutic effects in pill or injection forms, but they are no or little effective when applied to the site of infection as an ointment ("Antiviral Research", Vol. 14, pp. 305-321 (1990)).

Among antiviral agents other than the nucleic acid type antiviral agents and agents effective against DNA viruses, for instance, phosphonoformate (PFA for short; see "Nippon Rinsho", Vol. 47 (2), pp. 390-394 (1989)), phosphonoacetate (PAA for short; see "Nippon Rinsho", Vol. 47 (2), pp. 390-394 (1989)) and cicloxolone ("Journal of Antimicrobial Chemotherapy", Vol. 18, Suppl. B. pp. 185-200 (1986)) have been known. However, problems with phosphonoformate and phosphonoacetate are that they have side effects such as renal disorders and anemia, whereas cicloxolone has not an antiviral activity high enough for therapy.

Groups of antiviral agents other than the nucleic acid type antiviral agents and agents effective against RNA viruses, for instance, amantadine ("Shonika Sinryo", Vol. 54(4), pp. 988-994 (1991)), remantadine ("Shonika Sinryo", Vol. 54(4), pp. 988-994 (1991)) and LY253963 (a thiadiazol derivative; "Shonika Sinryo", Vol. 54(4), pp. 988-994 (1991)) have been known. Amantadine and remantadine have been shown to be efficacious against influenza A virus but not against influenza B virus, and pose a grave problem—a side effect on the central nerve. LY253963 has been shown to be resistant to influenza viruses in animal tests, but its clinical efficacy has yet to be verified.

Recent knowledge of the gene structure of hepatitis C virus (HCV) that is a leading cause of post-transfusion hepatitis has indicated that it is a single stranded RNA virus having a full length of about 9.5 kilobases ("Science", Vol 244, pp. 359-362 (1989)). However, because HCV is a virus very likely to mutate and is not well understood how it replicates, the development of vaccines or anti-HCV drugs is still very slow ("Shindan To Tiryo", Vol. 80(2), pp. 295-302 (1992)).

For instance, AZT and DDI have been known as antiviral agents efficacious against retroviruses such as AIDS virus (HIV) ("Shonika Shinryo", Vol. 54(4), pp. 981-987 (1991)). However, these agents delay the development of AIDS, but cannot accelerate healing and have severe side effects such as myelopathy.

In recent years, patients with immunodeficiency diseases induced by organ transplantation, cancer chemotherapy and HIV infections have been increasing, posing a grave medical problem. Virus infections in such patients are so diverse in type that they cannot often be treated with existing antiviral drugs. Thus, the development of more improved antiviral drugs and of more efficacious antiviral drugs for HIV and HCV is required.

SUMMARY OF THE INVENTION

It is therefore a primary object of this invention to provide a novel glycyrrhetinic acid derivative which has an excellent antiviral action on herpes simplex virus, and an antiviral agent containing the glycyrrhetinic acid derivative as the main component.

We have first studied glycyrrhetinic acid derivatives to find the possibility of their being used as anti-ulcer and inflammatory drugs but, in the course thereof, we fortuitously discovered that compounds having various substituents at the 30-position of glycyrrhetinic acid or its derivatives have an excellent antiviral activity. Among them, a compound having a phenylpiperazine derivative at the 30-position of glycyrrhetinic acid or its derivative, i.e., 1-[3$\beta$-(3-carboxy-propanoyloxy)-18$\beta$-olean-12-en-30-yl]-4-(2-methoxyphenyl) piperazine, has been found to have a particularly high antiviral activity and be of greatly safety.

With a view of revealing the significance of phenylpiperazine or its related compounds bonded as substituents to the 30-position of glycyrrhetinic acid or its derivatives, we have studied the antiviral and cytotoxic actions of modified or unmodified phenylpiperazine, phenylpiperidine, phenylpyrrolidone, phenyltetrahydro-imidazole, phenylhomopiperazine, phenylaziridine, phenylazetidine, phenyldiazetidine and phenylperhydrozepine. Surprisingly enough, we have discovered that a number of compounds have a wide spectrum of antiviral actions on herpes simplex virus (types 1 and 2), vaccinia virus, influenza virus, and provide efficacious drugs for both topic and systemic therapies.

We have then investigated the antiviral activity of known compounds containing the above-mentioned modified or unmodified phenylpiperazine and its related compounds as substituents in their structures and novel compounds into which these compounds are introduced as substituents. Interestingly enough, we have thus discovered that many compounds have strong antiviral actions.

Based on such findings as mentioned above, we have strenously made intensive studies to achieve more improved antiviral activity than ever before. Consequently, we have discovered that compounds, which have saccharides at the 3-positions of glycyrrhetinic acid or its derivatives and modified or unmodified phenylpiperazine or its related compounds at the 30-position thereof, have very excellent antiviral actions and, at the same time, reduced or limited cytotoxic actions. This finding underlies the present invention.

DETAILED DESCRIPTION OF THE INVENTION

This invention provides novel glycerrhetinic acid derivatives having the following general formula (I).

General Formula (I)

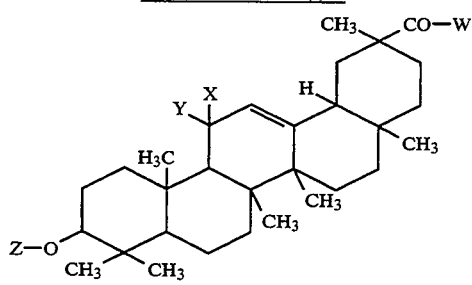

Here:
X and Y each represent a hydrogen atom or forms together an oxo group,
Z represents $A_2$—$(CH_2)_n$—$(CH=CH)_m$—$A_1$—, or a monosaccharide, disaccharide, oligosaccharide or polysaccharide or their derivative, and
W represents a substitutent expressed by —$OR_1$ where $R_1$ means a hydrogen atom, an alkyl, substituted alkyl or substituted alkenyl group, or a group having the following general formula (II)

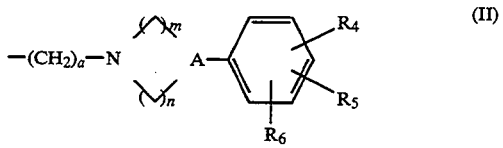

wherein A means a nitrogen atom or a methyne or methylene group, and $R_4$, $R_5$ and $R_6$ concurrently or independently mean a hydrogen atom, an amino group, an optionally substituted alkylamino group, an acylamino group, an optionally substituted alkyl group, a hydroxy group, an optionally substituted alkyloxy group, a halogeno group, a carboxy group, a formyl group, an optionally substituted alkylcarbonyl group, an optionally substituted alkoxycarbonyl, an aryloxycarbonyl group, an optionally substituted carbamoyl group, a nitro group, a cyano group, a thiol group, an optionally substituted alkylthio group, an optionally substituted phenyl group or an optionally substituted heteroring, m represents 0 or any desired integer, a and n each represent any desired integer, provided that the term "optionally substituted" means that said groups may be substituted by such groups as amino, formyl, hydroxy, alkoxy, aryloxy, halogeno, nitro, cyano, thiol, alkylthio, arylthio, acyl, carbamoyl, alkylsilyl, arylsilyl, alkyloxycarbonyl, aryloxycarbonyl, alkylsulfonyl, arylsulfonyl, alkylsulfinyl and arylsulfinyl groups, such acid groups as phosphoric, phosphonic, phosphinic, phosphenic, sulfonic, sulfinic, sulfuric and boric acid groups or their esters, and the term "heteroring" means pyridine, piperidine, piperazine, pyrrole, pyrrolidine, oxazole, imidazole, morpholine, diazole, triazole, tetrazole, thiazole and thiaziazole rings, by way of example, which may be condensed with benzene or each other, a substituent represented by -$NR_2R_3$ wherein $R_2$ and $R_3$ concurrently or independently represent a hydrogen atom, an alkyl, substituted alkyl or substituted alkenyl group, or a group having the general formula (III):

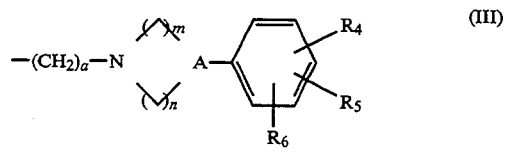

wherein A, $R_4$, $R_5$, $R_6$, a, m and n have the same meanings as defined above, a substituent represented by the following general formula (IV):

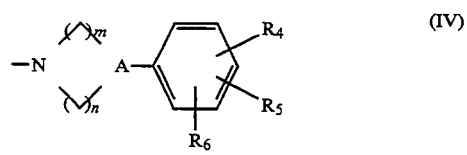

wherein A, $R_4$, $R_5$, $R_6$, m and n have the same meanings as defined above, or a substituent represented by the following general formula —NH—$(CH_2)$a-$A_3$-$R_7$ wherein a has the same meanings as defined above, $A_3$ denotes S, O or NH, and $R_7$ indicates an alkyl, alkenyl, phenyl or substituted phenyl group.

The glycyrrhetinic acid derivatives having General Formula (I) may be obtained in the form of glycosides by glycosylating a glycyrrhetinic acid derivative that is a compound itself known (as from Japanese Patent Laid-Open Publication No. 63-135351) in the art and represented by the following general formula (V):

General Formula (V)

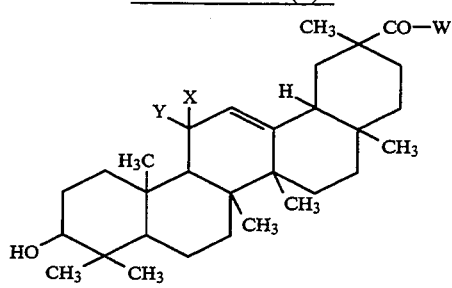

wherein X, Y and W have the same meanings as defined above, using glycosyl bromides as a saccharide donor according to conventional synthesis methods. For glycosylation to obtain the glycosides of glycyrrhetinic acid, for instance, the following Koenigs-Knorr type condensation may be used.

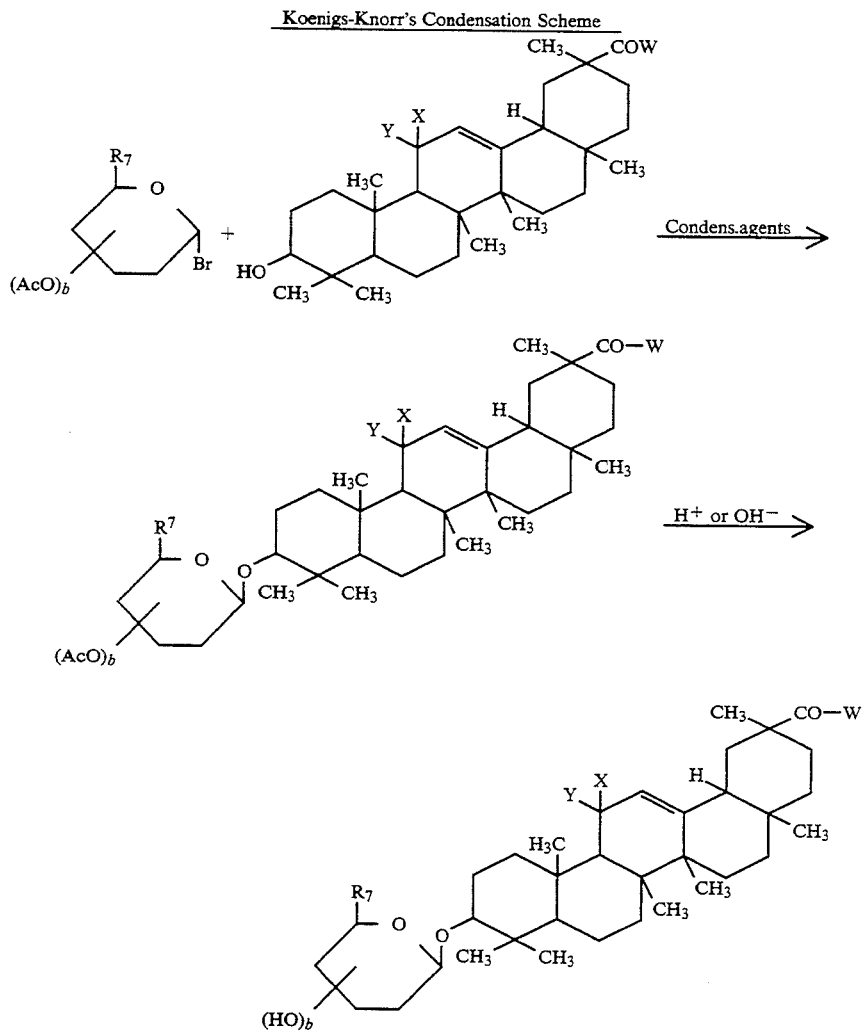

Here X, Y and W have the same meanings as defined above, $R_7$ stands for a carboxyl or hydroxymethyl group, and b is an any desired integer.

The saccharide donors used in this invention, for example, include glycosyl bromides of mono-, di-, oligo- and poly-saccharides or their derivatives. The glycosyl bromides of the monosaccharides, for instance, include those of glucose, fructose, mannose and ribose, of deoxymonosaccharides such as deoxyribose, of aminosaccharides such as glucosamine and mannosamine or of syalic or gluculonic acid. The glucosyl bromides of the disaccharides, for instance, include those of cane sugar, glucuronylglucuronic acid and syalyl-glucose. The glycosyl bromides of cyclodextrin, oligosaccharides and polysaccharides may be used as well.

By sulfation or phosphation of the thus produced glycosides of the glycyrrhetinic acid derivatives in conventional manners, it may also be possible to obtain the sulfated or phosphated products thereof.

The glycyrrhetinic acid derivatives represented by General Formula (I) according to this invention have strong antiviral action and low toxicity, and may be provided in the form of various pharmaceutical formulations for systemic therapy. The glycyrrhetinic acid derivatives represented by General Formula (I) have a surface active action in themselves, and so may produce good effects by themselves, when topically applied to the site of infection. However, their effects can be more enhanced in combination with absorption enhancers.

Set out below are preferred examples of the de novo compounds of this invention which turn out to provide efficacious antiviral agents.

(a) 1-(3β-(2,3,4,6-tetra-O-acetyl-β-D-glucopyranosyloxy)-18β-olean-12-en-30-oyl)-4-(2-methoxyphenyl)piperazine (b) 1-(3β-(β-D-glucopyranosyloxy)-18β-olean-12-en-30-oyl)-4-(2-methoxyphenyl)piperazine (c) 1-(3β-(β-D-glucopyranosyloxy)-11-oxo-18β-olean-12-en-30-oyl)-4-(2-methoxyphenyl)piperazine (d) 1-(3β-(β-D-glucopyranosyloxy)-18β-olean-12-en-30-oyl)-4-(2-chlorophenyl)piperazine (e) 1-(3β-(β-D-glucopyranosyloxy)-11-oxo-18β-olean-12-en-30-oyl)-4-(2-chlorophenyl)piperazine (f) 1-(3β-(β-D-glucopyranosyloxy)-18β-olean-12-en-30-oyl)-4-(2-trifluoromethylphenyl)piperazine (g) 1-(3β-(β-D-glucopyranosyloxy)-11-oxo-18β-olean-12-en-30-oyl)-4-(2-trifluoromethylphenyl)piperazine (h) 1-(3β-(β-D-glucopyranosyloxy)-18β-olean-12-en-30-oyl)-4-(2,6-dichlorophenyl)piperazine (i) 1-(3β-(β-D-glucopyranosyloxy)-11-oxo-18β-olean-12-en-30-oyl)-4-(2,6-dichlorophenyl)piperazine (j) 3β-(β-D-glucopyranosyloxy)-N-(2-(4-(2-methoxyphenyl) piperazine-1-yl)ethyl)-18β-olean-12-en-30-amide (k) 3β-(β-D-glucopyranosyloxy)-N-(2-(4-(2-methoxyphenyl) piperazine-1-yl)ethyl)-11-oxo-18β-olean-12-en-30-amide (l) 3β-(β-D-glucopyranosyloxy)-N-(2-(4-(2-chlorophenyl) piperazine-1-yl)ethyl)-18β-olean-12-en-30-amide (m) 3β-(β-D-glucopyranosyloxy)-N-(2-(4-(2-chlorophenyl) piperazine-1-yl)ethyl)-11-oxo-18β-olean-12-en-30-amide (n) 30-(N-(2-(4-(2-methoxyphenyl)piperazine-1-yl)carbonyl-18β-olean-12-en-3β-yl-2-O-β-D-glucuronyl-α-D-glucuronic acid (o) 3β-O-(2,4,6-tri-O-sulfonate)-β-D-glucopyrasyl-11-oxo-18β-olean-12-en-30-oic acid Salts of Compounds (a)–(n) are useful as well. Particularly efficacious compounds which have been found to haven antiviral action are enumerated in Table 1 just below.

Table 1

(1) 1-(3β-acetoxy-18β-olean-12-en-30-oyl)-4-(2-methoxyphenyl) piperazine, m.p.: 210°–212° C.; MS spectrum: (ED/DI)m/z: 672(M+, base peak).

(2) 1-(3β-acetoxy-18β-olean-12-en-30-oyl)-4-(3,7,11-trimethyl-2,6,10-dodecatrien-1-yl)piperazine, m.p.: powders; MS spectrum: (ED/DI)m/z: 770(M+), 69(base peak).

(3) 1-(3β-acetoxy-11-oxo-18β-olean-12-en-30-oyl)-4-(2-methoxyphenyl)piperazine, m.p.: powders; MS spectrum: (ED/DI) m/z: 686(M+), 149(base peak).

(4) N-[2-(3,7,11-trimethyl-2,6,10-dodecatrien-1-ylthio)ethyl]-3β-acetoxy-18β-olean-12-en-30-amide, m.p.: 80°–85° C., MS spectrum: (ED/DI)m/z: 775(M+), 572(base peak).

(5) 1-[3β-(3-carboxy-cis-propenoyloxy)-18β-olean-12-en-30-oyl]-4-(2-methoxyphenyl)piperazine.

(6) 1-(3β-hydroxy-18β-olean-12-en-30-oyl)-4-(3,7,11-trimethyl-2,6,10-dodecatrien-1-yl)piperazine, m.p.: 102°–105° C., MS spectrum: (ED/DI)m/z: 728(M+, base peak).

(7) 1-(3β-hydroxy-11-oxo-18β-olean-12-en-30-oyl)-4-(3,7,11-trimethyl-2,6,10-dodecatrien-1-yl)piperazine, m.p.: 179°–182° C., MS spectrum: (ED/DI)m/z: 644(M+), 149(base peak).

(8) N-[2-(3,7,11-trimethyl-2,6,10-dodecatrien-1-ylthio)ethyl]-3β-acetoxy-11-oxo-18β-olean-12-en-30-amide, m.p.: 75°–75° C., MS spectrum: (ED/DI)m/z: 734(M+), 531(base peak).

(9) 1-(3β-hydroxy-18β-olean-12-en-30-oyl)-4-(2-methoxyphenyl) piperazine, m.p.: 191°–193° C., MS spectrum: (ED/DI)m/z: 611(base peak).

(10) 1-[3β-carboxy-cis-propenoyloxy)-18β-olean-12-en-30-oyl]-4-(3,7,11-trimethyl-2,6,10-dodecatrien-1-yl)piperazine, m.p.: 136°–138° C., MS spectrum: (ED/DI)m/z: 729(M+−97), 69(base peak).

(11) 1-[3β-(3-carboxy-cis-propenoyloxy)-11-oxo-18β-olean-12-en-30-oyl]-4-(2-methoxyphenyl)piperazine, m.p.: 168°–171° C., MS spectrum: (ED/DI)m/z: 742(M+), 149(base peak).

(12) N-[2-3,7,11-trimethyl-2,6,10-dodecatrien-1-ylthio)ethyl]-3β-(3-carboxy-cis-propenoyloxy)-11-oxo-18β-olean-12-en-30-amide, m.p.: 75°–80° C., MS spectrum: (ED/DI)m/z: 734(M+−98), 69(base peak).

(13) 1-[3β-(3-carboxypropanoyloxy)-18β-olean-12-en-30-oyl]-4-(2-methoxyphenyl)piperazine, m.p.: 198°–200° C., MS spectrum: (ED/DI)m/z: 734(M+−98), 612(base peak).

(14) methyl-3β-(2-carboxyethoxymethoxy)-18β-olean-12-en-30-oate, m.p.: 155°–156° C., MS spectrum: (ED/DI)m/z: 556(M+), 262(base peak).

(15) disodium-3β-carboxymethoxy-18β-olean-12-en-30-oate, m.p.: 310°–312° C. (dec.).

(16) 3β-carboxymethoxy-18β-olean-12-en-30-oic acid, MS spectrum: (ED/DI)m/z: 509(M+), 248(base peak).

(17) 3β-(2-carbamoylethoxy)-18β-olean-12-en-30-oic acid, m.p.: 290°–291° C. (dec.), MS spectrum: (ED/DI)m/z: 527(M+), 248(base peak).

(18) disodium-3β-(2-carboxyethoxy)-18β-olean-12-en-30-oate, m.p. 295°–300° C. (dec.).

The compounds of this invention may be orally administrated to patients with viral diseases in liquid, tablet, capsule, (fine) granule, buccal tablet, troche and other forms, which may be prepared according to conventional manners. If desired, they may be used in combination with absorption enhancers such as bile salts, saponins and polyoxyethylene higher alcohol ethers. Although varying depending upon the type of the compounds, the conditions of patients, the form of preparations, etc., they may generally be administrated to the patients in doses lying in the range of 10 to 5000 mg a day.

The compounds of this invention may be formulated in injection forms by conventional manner as well. In this case, they may generally be administrated to human patients in doses of 30 to 3000 mg a day, although depending upon the type of the compounds and the conditions of the patients.

For topic therapy, the compounds of this invention may be formulated in liquid, ointment, cream, hydrogel, suppository (for both the rectum and vagina) forms, and may be prepared as eye lotion and ointment as well. These drugs may be prepared in conventional manners and, if desired, may be used in combination with absorption enhancers such as bile salts, saponins and polyoxyethylene higher alcohol ethers, polethylene glycol, DMSO and laurocaplam. Although varying with the type of the compounds, the conditions of human patients, the form of preparations, etc., these drugs may contain the compounds in amounts of 0.01 to 10%.

EXAMPLES

The present invention will now be explained more specifically but not exclusively with reference to examples of compound production, pharmacological tests and pharmaceutical compositions.

Example 1

1-(3β-acetoxy-18β-olean-12-en-30-oyl)-4-(2-methoxyphenyl) piperazine (1a)

To a solution of 3β-acetoxy-18β-olean-12-en-30-oyl chloride (15.0 g, 29.1 mmol) and triethylamine (2.94 g, 29.1 mmol) in dichloromethane (200 ml), 1-(2-methoxyphenyl) piperazine (5.59 g, 29.1 mmol) was added, followed by stirring for 2 hours at 10°–20° C.

The reaction mixture was washed with water, dried over sodium sulfate, and concentrated in vacuo. The residue was purified by silica gel column chromatography (dichloromethane) to obtain 19.3 g (98.6%) of the desired compound having the following physical properties. Melting Point: 210°–212° C., and Mass Spectrum (EI/DI)m/z: 672 (M+, base peak)

Example 2

1-(3β-acetoxy-18β-olean-12-en-30-oyl)-4-(2-chlorophenyl) piperazine (1b)

This compound was prepared by following the procedure of Example 1 with the exception that 1-(2-chlorophenyl)piperazine was used instead of 1-(2-methoxylphenyl)piperazine. Mass Spectrum (EI/DI)m/z: 676 (M+), 189 (base peak)

Example 3

1-(3β-acetoxy-18β-olean-12-en-30-oyl)-4-(2-trifluoromethylphenyl)piperazine (1c)

This compound was prepared by following the procedure of Example 1 with the exception that 1-(2-trifluoromethylphenyl) piperazine was used instead of 1-(2-methoxyphenyl)piperazine. Mass Spectrum (EI/DI)m/z: 710 (M+, base peak)

Example 4

1-(3β-acetoxy-18β-olean-12-en-30-oyl)-4-(2,6-dichlorophenyl) piperazine (1d)

This compound was prepared by following the procedure of Example 1 with the exception that 1-(2,6-dichlorophenyl) piperazine was used instead of 1-(2-methoxyphenyl)piperazine. Mass Spectrum (EI/DI)m/z: 710(M+, base peak)

Example 5

3β-acetoxy-N-(2-4-(2-methoxyphenyl)piperazine-1-yl)ethyl)-18β-olean-12-en-30-amide (1e)

This compound was prepared by following the procedure of Example 1 with the exception that 1-(2-aminoethyl)-4-(2-methoxyphenyl) piperazine was used instead of 1-(2-methoxyphenyl)piperazine. Mass Spectrum (EI/DI)m/z: 715(M+), 205(base peak)

Example 6

3β-acetoxy-N-(2-4-(2-chlorophenyl)piperazine-1-yl)ethyl)-18β-olean-12-en-30-amide (1f)

This compound was prepared by following the procedure of Example 1 with the exception that 1-(2-aminoethyl)-4-(2-methoxyphenyl)piperazine was used instead of 1-(2-methoxyphenyl)piperazine. Mass Spectrum (EI/DI)m/z: 719(M+), 205(base peak)

Example 7

1-(3β-acetoxy-11-oxo-18β-olean-12-en-30-oyl)-4-(2-methoxyphenyl)piperazine (2a)

To a solution of 3β-acetoxy-11-oxo-18β-olean-12-en-30-oyl chloride (26.6 g, 50.0 mmol) and triethylamine (5.06 g, 550.0 mmol) in dichloromethane (400 ml), 1-(2-methoxyphenyl) piperazine (9.60 g, 50.0 mmol) was added, followed by stirring for 2 hours at 10°–20° C.

The reaction mixture was washed with water, dried over sodium sulfate, and concentrated in vacuo. The residue was purified by silica gel column chromatography (dichloromethane) to give 34.4 g (100%) of the desired compound in the form of colorless powders. Mass spectrum (EI/DI)m/z: 686 (M+, base peak)

Example 8

1-(3β-acetoxy-11-oxo-18β-olean-12-en-30-oyl)-4-(2-chlorophenyl)piperazine (2b)

This compound was prepared by following the procedure of Example 7 with the exception that 1-(2-trifluoromethylphenyl) piperazine was used instead of 1-(2-methoxyphenyl)piperazine. Mass spectrum (EI/DI)m/z: 690 (M+, base peak)

Example 9

1-(3β-acetoxy-11-oxo-18β-olean-12-en-30-oyl)-4-(2-trifluoromethylphenyl)piperazine (2c)

This compound was prepared by following the procedure of Example 7 with the exception that 1-(2-trifluoromethylphenyl) piperazine was used instead of 1-(2-methoxyphenyl)piperazine. Mass spectrum (EI/DI)m/z: 724 (M+, base peak)

Example 10

1-(3β-acetoxy-11-oxo-18β-olean-12-en-30-oyl)-4-(2,6-dichlorophenyl)piperazine (2d)

This compound was prepared by following the procedure of Example 7 with the exception that 1-(2,6-dichrolophenyl) piperazine was used instead of 1-(2-methoxyphenyl)piperazine. Mass spectrum (EI/DI)m/z: 724 (M+, base peak)

Example 11

3β-acetoxy-N-(2-4-(2-methoxyphenyl)piperazine-1-yl)ethyl)-11-oxo-18β-olean-12-en-30-amide(2e)

This compound was prepared by following the procedure of Example 7 with the exception that 1-(2-aminoethyl)-4-(2-methoxyphenyl) piperazine was used instead of 1-(2-methoxyphenyl)piperazine. Mass spectrum (EI/DI)m/z: 729 (M+) 205(base peak).

Example 12

3β-acetoxy-N-(2-4-(2-chlorophenyl)piperazine-1-yl)ethyl)-11-oxo-18β-olean-12-en-30-amide(2f)

This compound was prepared by following the procedure of Example 7 with the exception that 1-(2-aminoethyl)-4-(2-chlorophenyl) piperazine was used instead of 1-(2-methoxyphenyl)piperazine. Mass spectrum (EI/DI)m/z: 733 (M+, base peak).

Example 13

1-(3β-hydroxy-18β-olean-12-en-30-oyl-4-(2-methoxyphenyl) piperazine(3a)

To a solution of 1-(3β-acetoxy-18β-olean-12-en-30-oyl)-4-(2-methoxyphenyl)piperazine(1a)(17.5 g, 26.0 mmol, obtained in Example 1) in 1,4-dioxane(100 ml), 20% NaOH/methanol(100 ml) was added, followed by stirring for 5 hours at 20° C.

The reaction mixture was poured into ice water and then extracted with chloroform (150 ml×2). The resulting organic layer was collected, washed with a saturated NaCl solution, dried over sodium sulfate, and concentrated in vacuo. The residue was purified by silica gel column chromatography (5% diethyl ether/dichloromethane) to give 13.3 g(81.0%) of the desired compound having the following physical data. Melting point: 219°–220° C. Mass spectrum (EI/DI)m/z: 630 (M+), 149(base peak).

Example 14

1-(3β-hydroxy-18β-olean-12-en-30-oyl)-4-(2-chlorophenyl) piperazine (3b)

This compound was prepared by following the procedure of Example 13 with the exception that 1-(3β-acetoxy-18β-olean-12-en-30-oyl)-4-(2-methoxyphenyl)piperazine(1b) (obtained in Example 2) was used instead of 1-(3β-acetoxy-18β-olean-12-en-30-oyl)-4-(2-methoxyphenyl))piperazine (1a). Mass spectrum (EI/DI)m/z: 634 (M+), 189(base peak).

Example 15

1-(3β-hydroxy-18β-olean-12-en-30-oyl)-4-(2-trifluoromethylphenyl)piperazine (3c)

This compound was prepared by following the procedure of Example 13 with the exception that 1-(3β-acetoxy-18β-olean-12-en-30-oyl)-4-(2-trifluoromethylphenyl)piperazine(1c) (obtained in Example 3) was used instead of 1-(3β-acetoxy-18β-olean-12-en-30-oyl)-4-(2-methoxyphenyl)piperazine (1a). Mass spectrum (EI/DI)m/z: 668 (M+), 189(base peak).

Example 16

1-(3β-hydroxy-18β-olean-12-en-30-oyl)-4-(2,6-dichlorophenyl) piperazine (3d)

This compound was prepared by following the procedure of Example 13 with the exception that 1-(3β-acetoxy-18β-olean-12-en-30-oyl)-4-(2,6-dichlorophenyl)piperazine(1d) (obtained in Example 4) was used instead of 1-(3β-acetoxy-18β-olean-12-en-30-oyl)-4-(2-methoxyphenyl)piperazine (1a). Mass spectrum (EI/DI)m/z: 668 (M+, base peak).

Example 17

3β-hydroxy-N-(2-4-(2-methoxyphenyl)piperazine-1-yl)ethyl)-18β-olean-12-en-30-amide(3e)

This compound was prepared by following the procedure of Example 13 with the exception that 3β-acetoxy-N-(2-4-(2-methoxyphenyl)piperazine-1-yl)ethyl-18β-olean-12-en-30-amide(1e) (obtained in Example 5) was used instead of 1-(3β-acetoxy-18β-olean-12-en-30-oyl)-4-(2-methoxyphenyl)piperazine (1a). Mass spectrum (EI/DI)m/z: 673 (M+), 205(base peak).

Example 18

3β-hydroxy-N-(2-4-(2-chlorophenyl)piperazine-1-yl)ethyl)-18β-olean-12-en-30-amide (3f)

This compound was prepared by following the procedure of Example 13 with the exception that 3β-acetoxy-N-(2-4-(2-chlorophenyl)piperazine-1-yl)ethyl-18β-olean-12-en-30-amide (1f) (obtained in Example 6) was used instead of 1-(3β-acetoxy-18β-olean-12-en-30-oyl)-4-(2-methoxyphenyl)piperazine (1a). Mass Spectrum (EI/DI)m/z: 677(M+), 209(base peak).

Example 19

1-(3β-hydroxy-11-oxo-18β-olean-12-en-30-oyl)-4-(2-methoxyphenyl)piperazine (4a)

To a solution of 1-(3β-acetoxy-11-oxo-18β-olean-12-en-30-oyl)-4-(2-methoxyphenyl)piperazine (2a) (31.8 g, 46.4 mmol, obtained in Example 7) in 1,4-dioxane (360 ml), 5% NaOH/methanol (360 ml) was added, followed by stirring for 3 hours at 20° C.

The reaction mixture was poured into ice water and then extracted with chloroform (500 ml×2). The organic layer was collected, washed with a saturated NaCl solution dried over sodium sulfate, and concentrated in vacuo. The residue was purified by silica gel column chromatography (5% diethyl ether/dichloromethane) to give 22.9 g (76.6%) of the desired compound having the following physical data. Melting Point: 179°–182° C.; Mass Spectrum (EI/DI)m/z: 644(M+), 149(base peak).

Example 20

1-(3β-hydroxy-11-oxo-18β-olean-12-en-30-oyl)-4-(2-chlorophenyl)piperazine (4b)

This compound was prepared by following the procedure of Example 19 with the exception that 1-3β-acetoxy-11-oxo-18β-olean-12-en-30-oyl)-4-(2-chlorophenyl)piperazine (2b) (obtained in Example 18) was used instead of 1-(3β-acetoxy-11-oxo-18β-olean-12-en-30-oyl)-4-(2-methoxyphenyl)piperazine (2a). Mass Spectrum (EI/DI)m/z: 648(M+, base peak).

Example 21

1-(3β-hydroxy-11-oxo-18β-olean-12-en-30-oyl)-4-(2-trifluoromethylphenyl)piperazine (4c)

This compound was prepared by following the procedure of Example 19 with the exception that 1-3β-acetoxy-11-oxo-18β-olean-12-en-30-oyl)-4-(2-trifluoromethylphenyl)piperazine (2c) (obtained in Example 18) was used instead of 1-(3β-acetoxy-11-oxo-18β-olean-12-en-30-oyl)-4-(2-methoxyphenyl)piperazine (2a). Mass Spectrum (EI/DI)m/z: 682(M+, base peak).

Example 22

1-(3β-hydroxy-11-oxo-18β-olean-12-en-30-oyl)-4-(2,6-dichlorophenyl)piperazine (4d)

This compound was prepared by following the procedure of Example 19 with the exception that 1-3β-acetoxy-11-oxo-18β-olean-12-en-30-oyl)-4-(2,6-dichlorophenyl)piperazine (2d) (obtained in Example 18) was used instead of 1-(3β-acetoxy-11-oxo-18β-olean-12-en-30-oyl)-4-(2-methoxyphenyl)piperazine (2a). Mass Spectrum (EI/DI)m/z: 682(M+, base peak).

Example 23

3β-hydroxy-N-(2-4-(2-methoxyphenyl)piperazine-1-yl)ethyl)-11-oxo-18β-olean-12-en-30-amide (4e)

This compound was prepared by following the procedure of Example 19 with the exception that 3β-acetoxy-N-(2-4-(2-methoxyphenyl)piperazine-1-yl)ethyl-11-oxo-18β-olean-12-en-30-amide (2e) (obtained in Example 11) was used instead of 1-(3β-acetoxy-11-oxo-18β-olean-12-en-30-oyl)-4-(2-methoxyphenyl)piperazine (2a). Mass Spectrum (EI/DI)m/z: 687(M+), 205(base peak).

Example 24

3β-hydroxy-N-(2-4-(2-chlorophenyl)piperazine-1-yl)ethyl)-11-oxo-18β-olean-12-en-30-amide (4f)

This compound was prepared by following the procedure of Example 19 with the exception that 3β-acetoxy-N-(2-4-(2-chlorophenyl)piperazine-1-yl)ethyl-11-oxo-18β-olean-12-en-30-amide (2f) (obtained in Example 12) was used instead of 1-(3β-acetoxy-11-oxo-18β-olean-12-en-30-oyl)-4-(2-methoxyphenyl)piperazine (2a). Mass Spectrum (EI/DI)m/z: 691(M+, base peak).

Example 25

1-(3β-(β-D-glucopyranosyloxy)-18β-olean-12-en-30-oyl)-4-(2-methoxyphenyl)piperazine (5a)

A mixture of 1-(3β-hydroxy-18β-olean-12-en-30-oyl)-4-(2-methoxyphenyl)piperazine (1a) (4.00 g, 6.34 mmol, obtained in Example 13), drierite (16.0 g, 0.118 mmol), iodine (0.800 g, 6.30 mmol), Ag$_2$O (14.7 g, 63.4 mmol), and absolute chloroform (80 ml) was stirred for 30 minutes at 20° C. Then, to the mixture, a solution of tetra-O-acetyl-α-D-glucopyranosyl bromide in absolute chloroform (80 ml) was added over 10 minutes, followed by stirring for 24 hours at 20° C.

The reaction mixture was concentrated in vacuo. The residue was purified by silica gel column chromatography (5% diethyl ether/dichloromethane) to give 5.28 g (91.2%) of 1-(3β-(2,3,4,6-tetra-O-acetyl-β-D-glucopyranoxyloxy)-18β-olean-12-en-30-oyl)-4-(2-methoxyphenyl)piperazine(5'a) having the following physical data.

The obtained 5'a was dissolved in a mixture of chloroform and methanol (3:1), and to the mixture 0.1M sodium methoxide (300 ml,30 mmol) was added, followed by stirring for 15 hours at 20° C. The reaction mixture was regulated to pH5-6 with 5% HCl and concentrated in vacuo. The residue was extracted with chloroform (400 ml) and water (400 ml). The organic layer were collected, dried over sodium sulfate, and concentrated in vacuo. The residue was purified by silica gel column chromatography (chloroform:diethyl ether=10:1-chloroform:methanol=20:1) to give 4.34 g(86.3%) of the desired compound having the following physical data, as colorless powders.

(5'a)

$^1$H-NMR spectrum (CDCl$_3$) δ ppm: 0.80,0.87,0.88,0.96,1.13,1.23(21H,sx6,CH$_3$x7),1.2–2.2(2-3H,m,CH and CH$_2$),2.01,2.02,22.0(12H,sx6,CH$_3$COx4),3.05(4H,brs,C-H$_2$x2), 3.15(1H,brs,C$_3$-H),3.2–3.7(3H,m,C'$_5$-H and C'$_6$-H),3.7–3.9(4H,m,CH$_2$x2),3.88(3H,-s,OCH$_3$),4.34(2H,brs,C'$_2$-H and C'$_4$-H),4.92(1H,brs,C'$_1$-H),5.21(1H,brs,C'$_3$-H),5.3–5.4(1H,m,C$_{12}$-H),6.9–7.4(4H,m,aromatic H)

(5a)

$^1$H-NMR spectrum (CDCl$_3$) δ ppm: 0.80,0.87,0.88,0.96,1.13,1.23(21H,sx6,CH$_3$x7),1.2–2.2(2-3H,m,CH and CH$_2$),3.05(4H,brs,CH$_2$x2),3.15(1H,brs,C$_3$-H),3.2–3.7(3H,m,C'$_5$-H and C'$_6$-H),3.7–3.9(4H,m,CH$_2$x2),3.88(3H,s,OCH$_3$), 4.34(2H,brs, C'$_2$-H and C'$_4$-H),4.92(1H,brs,C'$_1$-H),5.21(1H,brs,C'$_3$-H),5.3–5.4(1H,m,C$_{12}$-H),6.9–7.4(4H,m,aromatic H)

Example 26

1-(3β-(β-D-glucopyranosyloxy)-18β-olean-12-en-30-oyl)-4-(2-chlorophenyl)piperazine (5b)

This compound was prepared by following the procedure of Example 25 with the exception that 1-(3β-hydroxy-18β-olean-12-en-30-oyl)-4-(2-chlorophenyl)-piperazine(3b) (obtained in Example 14) was used instead of 1-(3β-hydroxy-18β-olean-12-en-30-oyl)-4-(2-methoxyphenyl)piperazine(3a).

$^1$H-NMR spectrum (CDCl$_3$) δ ppm: 0.79,0.81,0.94,0.96,1.00,1.14,1.23(21H,sx7,CH$_3$x7),0.8–2.1(23H,m,CH and CH$_2$),3.03(4H,brs,CH$_2$x2),3.15(1H,brs,C$_3$-H),3.2–3.7(3H,m,C'$_5$-H and C'$_6$-H),3.7–3.9(4H,m,CH$_2$x2),4.34(2H,brs,C'$_2$-H and C'$_4$-H),4.92(1H,brs,C'$_1$-H),5.21(1H,brs,C'$_3$-H),5.3–5.4(1H,m,C$_{12}$-H),7.0–7.4(4H,m,aromatic H)

Example 27

1-(3β-(β-D-glucopyranosyloxy)-18β-olean-12-en-30-oyl)-4-(2-trifluoromethylphenyl)piperazine(5c)

This compound was prepared by following the procedure of Example 25 with the exception that 1-(3β-hydroxy-18β-olean-12-en-30-oyl)-4-(2-trifluoromethylphenyl)piperazine(3c) (obtained in Example 15) was used instead of 1-(3β-hydroxy-18β-olean-12-en-30-oyl)-4-(2-methoxyphenyl)piperazine(3a).

$^1$H-NMR spectrum (CDCl$_3$) δ ppm: 0.79,0.82,0.95,0.97,1.00,1.14,1.23(21H,sx7,CH$_3$x7),0.7–2.1(23H,m,CH and CH$_2$),2.8–3.0(4H,brs,CH$_2$x2),3.20(1H,brs,C$_3$-H), 3.2–3.7(3H,m,C'$_5$-H and C'$_6$-H),3.7–3.9(4H,m,CH$_2$x2), 4.34(2H,brs,C'$_2$-H and C'$_4$-H),4.92(1H,brs,C'$_1$-H),5.21(1H,brs, C'$_3$-H),5.3–5.4(1H,m,C$_{12}$-H),7.2–7.6(4H,m,aromatic H)

Example 28

1-(3β-(β-D-glucopyranosyloxy)-18β-olean-12-en-30-oyl)-4-(2,6-dichlorophenyl)piperazine(5d)

This compound was prepared by following the procedure of Example 25 with the exception that 1-(3β-hydroxy-18β-olean-12-en-30-oyl)-4-(2,6-dichlorophenyl)piperazine(3d) (obtained in Example 16) was used instead of 1-(3β-hydroxy-18β-olean-12-en-30-oyl)-4-(2-methoxyphenyl)piperazine(3a).

$^1$H-NMR spectrum (CDCl$_3$) δ ppm: 0.79,0.81,0.94,0.96,1.00,1.14,1.23(21H,sx7,CH$_3$x7),0.8–2.1(23H,m,CH and CH$_2$),3.03(4H,brs,CH$_2$x2),3.15(1H,brs,C$_3$-H),3.2–3.7(3H,m,C'$_5$-H and C'$_6$-H),3.7–3.9(4H,m,CH$_2$x2), 4.34(2H,brs,C'$_2$-H and C'$_4$-H),4.92(1H,brs,C'$_1$-H),5.21(1H,brs, C'$_3$-H),5.3–5.4(1H,m,C$_{12}$-H),7.2–7.4(3H,m,aromatic H)

Example 29

3β-(β-D-glucopyranosyloxy)-N-(2-4-(2-methoxyphenyl)piperazine-1-yl)ethyl-18β-olean-12-en-30-amide (5e)

This compound was prepared by following the procedure of Example 25 with the exception that 3β-hydroxy-N-(2-4-(2-methoxyphenyl)piperazine-1-yl)ethyl-18β-olean-12-en-30-amide(3e) (obtained in Example 17) was used instead of 1-(3β-hydroxy-18β-olean-12-en-30-oyl)-4-(2-methoxyphenyl) piperazine(3a).

$^1$H-NMR spectrum (CDCl$_3$) δ ppm: 0.79,0.91,0.95,1.00,1.11,1.15(21H,sx6,CH$_3$x7),0.7–2.1(2-3H,m,CH and CH$_2$),2.5–2.6(2H,m,CH$_2$),2.6–2.8(4H,m,,piperazine), 3.15(1H,m,C$_3$-H),3.0–3.2(4H,m,,piperazine),3.2–3.7(3H,m,C'$_5$-H and C'$_6$-H),3.3–3.5(2H,m,CH$_2$),3.87(3H,-s,OCH$_3$),4.34(2H,brs,C'$_2$-H and C'$_4$-H),4.92(1H,brs,C'$_1$-H),5.21(1H,brs,C'$_3$-H),5.41(1H,m,C$_{12}$-H),6.45(1H,brs,CONH),6.8–7.1(4H,m,aromatic H)

Example 30

3β-(β-D-glucopyranosyloxy)-N-(2-4-(2-chlorophenyl)-piperazine-1-yl)ethyl-18β-olean-12-en-30-amide (5f)

This compound was prepared by following the procedure of Example 25 with the exception that 3β- hydroxy-N-(2-4-(2-chlorophenyl)piperazine-1-yl)ethyl-18β-olean-12-en-30-amide(3f) (obtained in Example 18) was used instead of 1-(3β-hydroxy-18β-olean-12-en-30-oyl)-4-(2-methoxyphenyl) piperazine(3a).

$^1$H-NMR spectrum (CDCl$_3$) δ ppm: 0.79,0.82,0.94,0.97,1.00,1.14,1.22(21H,sx7,CH$_3$x7),0.8–2.1(23H,m,CH and CH$_2$),2.5–2.6(2H,m,CH$_2$),2.6–2.8(4H,m, piperazine),3.15(1H,m,C$_3$-H),3.0–3.2(4H,m,piperazine),3.2–3.7(3H,m,C'$_5$-H and C'$_6$-H),3.3–3.5(2H,m,CH$_2$),4.34(2H,brs,C'$_2$-H and C'$_4$-H),4.92(1H,brs,C'$_1$-H),5.21(1H,brs,C'$_3$-H),5.33(1H,m,C$_{12}$-H),6.45(1H,brs,CONH),7.0–7.4(4H,m,aromatic H)

Example 31

1-(3β-(β-D-glucopyranosyloxy)-11-oxo-18β-olean-12-en-30-oyl)-4-(2-methoxyphenyl)piperazine (6a)

This compound was prepared by following the procedure of Example 25 with the exception that 1-(3β-hydroxy-11-oxo-18β-olean-12-en-30-oyl)-4-(2-methoxyphenyl)piperazine (4a) (obtained in Example 19) was used instead of 1-(3β-hydroxy-18β-olean-12-en-30-oyl)-4-(2-methoxyphenyl) piperazine (3a).

$^1$H-NMR spectrum (CDCl$_3$) δ ppm: 0.82,0.89,0.91,0.98,1.15,1.26(21H,sx6,CH$_3$x7),1.2–2.2(21H,m,CH and CH$_2$),2.9–3.1(4H,brs,CH$_2$x2),3.16(1H,brs,C$_3$-H),3.2–3.7(3H,m,C'$_5$-H and C'$_6$-H),3.7–3.9(4H,m,CH$_2$x2),3.88(3H,s, OCH$_3$), 4.34(2H,brs,C'$_2$-H and C'$_4$-H),4.92(1H,brs,C'$_1$-H),5.21(1H,brs, C'$_3$-H),5.7–5.8(1H,m,C$_{12}$-H),7.0–7.5(4H,m,aromatic H)

Example 32

1-(3β-(β-D-glucopyranosyloxy)-11-oxo-18β-olean-12-en-30-oyl)-4-(2-chlorophenyl)piperazine (6b)

This compound was prepared by following the procedure of Example 25 with the exception that 1-(3β-hydroxy-11-oxo-18β-olean-12-en-30-oyl)-4-(2-chlorophenyl)piperazine(4b) (obtained in Example 20) was used instead of 1-(3β-hydroxy-18β-olean-12-en-30-oyl)-4-(2-methoxyphenyl)piperazine (3a).

$^1$H-NMR spectrum (CDCl$_3$) δ ppm: 0.81,0.83,0.97,0.99,1.02,1.16,1.25(21H,sx7,CH$_3$x7),0.8–2.1(21H,m,CH and CH$_2$),2.9–3.1(4H,m,CH$_2$x2),3.15(1H,brs,C$_3$-H),3.2–3.7(3H,m,C'$_5$-H and C'$_6$-H),3.7–3.9(4H,m,CH$_2$x2), 4.34(2H,brs,C'$_2$-H and C'$_4$-H),4.92(1H,brs,C'$_1$-H),5.21(1H,brs, C'$_3$-H),5.7–5.8(1H,m,C$_{12}$-H),7.1–7.5(4H,m,aromatic H)

Example 33

1-(3β-(β-D-glucopyranosyloxy)-11-oxo-18β-olean-12-en-30-oyl)-4-(2-trifluoromethylphenyl)piperazine(6c)

This compound was prepared by following the procedure of Example 25 with the exception that 1-(3β-hydroxy-11-oxo-18β-olean-12-en-30-oyl)-4-(2-trifluoromethylphenyl) piperazine(4c) (obtained in Example 21) was used instead of 1-(3β-hydroxy-18β-olean-12-en-30-oyl)-4-(2-methoxyphenyl) piperazine(3a).

$^1$H-NMR spectrum (CDCl$_3$) δ ppm: 0.81,0.84,0.97,0.99,1.02,1.16,1.25(21H,sx7,CH$_3$x7),0.7–2.1(21H,m,CH and CH$_2$),2.8–3.0(4H,m,CH$_2$x2),3.20(1H,brs,C$_3$-H),3.2–3.7(3H,m,C'$_5$-H and C'$_6$-H),3.7–3.9(4H,m,CH$_2$x2),4.34(2H,brs,C'$_2$-H and C'$_4$-H),4.92(1H,brs,C'$_1$-H),5.21(1H,brs, C'$_3$-H),5.7–5.8(1H,m,C$_{12}$-H),7.3–7.7(4H,m,aromatic H)

Example 34

1-(3β-(β-D-glucopyranosyloxy)-11-oxo-18β-olean-12-en-30-oyl)-4-(2',6-dichlorophenyl)piperazine (6c)

This compound was prepared by following the procedure of Example 25 with the exception that 1-(3β-hydroxy-11-oxo-18β-olean-12-en-30-oyl)-4-(2,6-dichlorophenyl) piperazine (4c) (obtained in Example 22) was used instead of 1-(3β-hydroxy-18β-olean-12-en-30-oyl)-4-(2-methoxyphenyl) piperazine(3a).

$^1$H-NMR spectrum (CDCl$_3$) δ ppm: 0.81,0.83,0.96,0.99,1.02,1.16,1.25(21H,sx7,CH$_3$x7),0.8–2.1(21H,m,CH and CH$_2$),2.8–3.0(4H,m,CH$_2$x2),3.15(1H,brs,C$_3$-H), 3.2–3.7(3H,m,C'$_5$-H and C'$_6$-H),3.7–3.9(4H,m,CH$_2$x2), 4.34(2H,brs,C'$_2$-H and C'$_4$-H),4.92(1H,brs,C'$_1$-H), 5.21(1H,brs, C'$_3$-H),5.7–5.8(1H,m,C$_{12}$-H),7.3–7.5(3H,m,aromatic H).

Example 35

3β-(β-D-glucopyranosyloxy)-N-(2-4-(2-methoxyphenyl)piperazine-1-yl)-ethyl)-11-oxo-18β-olean-12-en-30-amide (6e)

This compound was prepared by following the procedure of Example 25 with the exception that 3β-hydroxy-N-(2-4-(2-methoxyphenyl)piperazine-1-yl)ethyl)-11-oxo-18β-olean-12-en-30-amide (3e) (obtained in Example 23) was used instead of 1-(3β-hydroxy-18β-olean-12-en-30-oyl)-4-(2-methoxyphenyl) piperazine (3a).

$^1$H-NMR spectrum (CDCl$_3$) δ ppm: 0.81,0.93,0.97,1.02,1.13,1.17(21H,sx6,CH$_3$x7),0.7–2.1(2-1H,m,CH and CH$_2$),2.5–2.6(2H,m,CH$_2$), 2.6–2.8(4H, m, piperazine), 3.15 (1H, m, C$_3$-H) and C'$_6$-H), 3.0–3.2(4H, m, piperazine), 3.2–3.7(3H, m, C'$_5$-H and C'$_6$-H), 3.3–3.5(2H, m, CH$_2$), 3.87(3H, s, OCH$_3$), 4.34(2H, brs, C'$_2$-H and C'$_4$-H), 4.92(1H, brs, C'$_1$-H), 5.21(1H, brs, C'$_3$-H), 5.7–5.8(1H, m, C$_{12}$-H, 6.45(1H, brs, CONH), 6.9–7.2(4H, m, aromatic H).

Example 36

3β-(β-D-glucopyranosyloxy)-N-(2-4-(2-chlorophenyl)-piperazine-1-yl)ethyl)-11-oxo-18β-olean-12-en-30-amide (6f)

This compound was prepared by following the procedure of Example 25 with the exception that 3β-hydroxy-N-(2-4-(2-chlorophenyl)piperazine-1-yl)ethyl)-11-oxo-18β-olean-12-en-30-amide (3f) (obtained in Example 24) was used instead of 1-(3β-hydroxy-18β-olean-12-en-30-oyl)-4-(2-methoxyphenyl) piperazine (3a).

$^1$H-NMR spectrum (CDCl$_3$) δ ppm: 0.81, 0.85, 0.96, 0.99, 1.02, 1.16, 1.24(21H, sx7, CH$_3$x7), 0.8–2.1(21H, m, CH an CH$_2$), 2.5–2.6(2H, m, CH$_2$), 2.6–2.8(4H, m, piperazine), 3.15(1H, m, C$_3$-H), 3.0–3.2(4H, m, piperazine), 3.2–3.7(3H, m, C'$_5$-H and C'$_6$-H), 3.3–3.5(2H, m, CH$_2$), 4.34(2H, brs, C'$_2$-H and C'$_4$-H), 4.92(1H, brs, C'$_1$-H), 5.21(1H, brs, C'$_3$-H), 5.7–5.8(1H, m, C$_{12}$-H), 6.45(1H, brs, CONH), 7.0–7.4(4H, m, aromatic H).

Example 37

30-(N-2-(4-(2-methoxylphenyl)piperazine-1-yl)carbonyl)-18β-olean-12-en-3β-yl-2-O-β-D-glucuronyl-α-D-gluconic acid (7)

This compound was prepared by following the procedure of Example 25 with the exception that dimethyl-2,3-di-O-acetyl-1-bromo-deoxy-2-O-(2,3,4-tri-O-acetyl-β-D-glucuronyl)-α-D-glucuonic acid diester was used instead of tetra-O-acetyl-α-D-glucopyranosyl bromide.

The precipitate was filtered off, and the filtrate was concentrated in vacuo. The residue was refluxed in a solution of 5% NaOH:ethanol (3:1) for 3 hours, neutralized with Amberlite IR-120 (H+), and concentrated in vacuo. The residue was purified by silica gel column chromatography (chloroform:methanol=20:1) to give 2.64 g (41.6%) of the desired compound in the form of colorless powders.

$^1$H-NMR Spectrum (CDCl$_3$) δ ppm: 0.81, 0.88, 0.89, 0.97, 1.14, 1.24(21H, sx6, CH$_3$x7), 1.2–2.2(23H, m, CH and CH$_2$), 3.05(4H, brs, CH$_2$x2), 3.35(1H, brs, C$_3$-H), 3.2–3.7(2H, m, C'$_5$-H and C''$_5$-H), 3.7–3.9(4H, m, CH$_2$x2), 3.88(3H, s, OCH$_3$), 4.34(4H, brs, C'$_2$-H, C''$_2$-H, C'$_4$-H and C''$_4$-H), 4.92(2H, brs, C'$_1$-H and C''$_1$-H), 5.21(2H, brs, C'$_3$-H and C''$_3$-H), 5.3–5.4(1H, m, C$_{12}$-H), 6.9–7.4(4H, m, aromatic H).

Example 38

3β-(2,4,6-tri-O-sodiosulfonato-β-D-glucopyranosyloxy)-18β-olean-12-en-30-oic acid (8)

Sulfur trioxide pyridine complex (10.06 g) was added to a solution of 3β-(β-D-glucopyranosyloxy)-18β-olean-12-en-30-oic acid (5.00 g) in DMF (100 ml), followed by stirring for 17 hours at 20° C. The reaction mixture was poured into diethyl ether (500 ml), followed by stirring. The precipitated yellow oil was washed with dichloromethane (200 ml), dissolved in ion exchanged water, regulated to pH 5–6 with 1N NaOH, and lyophilized. The residue was purified by silica gel column chromatography to give 6.20 g (81.6%) of the desired compound in the form of colorless powders.

$^1$H-NMR spectrum (CDCl$_3$) δ ppm: 0.8(3H, s, CH$_3$), 0.86(3H, s, CH$_3$), 1.06(6H, s, CH$_3$x2), 1.13(&H, s, CH$_3$x2), 1.41(3H, s, CH$_3$), 2.50–2.60(1H, m, C$_{18}$-H), 2.55(1H, s, C$_9$-H), 3.30(1H, dd, J=10.74, 5.37 Hz, C$_3$-H), 4.16–4.26(2H, m, C$_5$-H, C$_{6b}$-H), 4.39(1H, dd, J=9.28, 6.84 Hz, C$_{6a}$-H), 4.49(1H, m, C$_2$-H), 4.61(1H, m, C$_4$-H), 4.82(1H, dd, J=4.88, 3.90 Hz, C$_3$-H), 4.91(1H, d. J=5.38 Hz, C$_1$-H), 5.70(1H, s, C$_{12}$-H).

Pharmacological Efficacy Testing - 1 Antiviral Action Against Herpes Simplex Virus Type 1 and Cytotoxicity For incubation, HSV-1 (Miyama strain) and the compounds to be tested were added to monolayers of GMK cells (derived from the kidney of a green monkey) grown on 97-holed culture plates. After incubation, the cytopathic effect (CPE) of the viruses as well as the effect of the compounds on CPE inhibition and on their cytotoxicity were microscopically observed. To estimate the antiviral action of the compounds, TCID$_{50}$ values were found using the GPE as an index and ΔTCID$_{50}$ (log$_{10}$) values were calculated by the TCID$_{50}$ values of both the compound-treated group and the control group. Bear in mind that prior to be added to the incubation systems, the compounds were regulated with MEM or ethanol media to 10 mg/ml concentrations, and diluted with MEM media containing 1% bovine fetus serum.

TABLE 2-1

In Vitro Antiviral Action of Compounds on Cells Infected with HSV-1(Miyama Strain)

| Compounds | Antiviral Activity (ΔTCID$_{50}$ (log$_{50}$)) | | |
|---|---|---|---|
| Comp. Concn. (μg/ml) | 1 | 5 | 25 |
| Comp. Ex. 25 | 1.86 (−) | >3.00 (−) | >3.56 (±) |
| Comp. Ex. 37 | 1.94 (−) | >3.17 (−) | >3.73 (−) |
| Table 1, Comp. | | | |
| (5) | 1.0 (−) | 2.1 (−) | 3.1 (−) |
| (9) | 1.3 (−) | 1.2 (+) | (++) |
| (10) | 0.7 (−) | 2.0 (+) | 1.9 (+) |
| (13) | 0.8 (−) | 2.6 (−) | 2.5 (+) |
| (15) | 0.0 (−) | 0.3 (−) | 1.0 (+) |
| (18) | 0.7 (−) | 1.6 (−) | 1.2 (+) |
| Carbenoxolone | 0.2 (−) | 0.3 (−) | 2.4 (+) |
| Ara-a | 1.2 (−) | 1.5 (+) | 2.5 (+) |

( ) stands for the magnitude of cytotoxicity [(−): no cytotoxicity, and (±): less cytotoxicity]

TABLE 2-2

Action of Compounds on HSV (UV-238 Strain)

| Compounds | Antiviral Activity (ΔTCID$_{50}$ (log$_{50}$)) | | |
|---|---|---|---|
| Comp. Concn. (μg/ml) | 1 | 5 | 25 |
| Table 1, Comp. | | | |
| (5) | 1.3 (−) | 2.2 (−) | 2.8 (−) |
| (9) | 0.7 (−) | 1.3 (+) | 2.5 (+) |
| (13) | 0.9 (−) | 1.4 (−) | 2.5 (+) |
| Carbenoxolone | 0.2 (−) | 0.2 (−) | 2.2 (+) |
| Ara-a | 1.1 (−) | 1.7 (+) | 2.6 (+) |

( ) stands for the magnitude of cytotoxicity [(−): no cytotoxicity, and (±): less cytotoxicity but antiviral activity found]

Pharmacological Efficacy Testing - 2 Antiviral Spectrum

For incubation, HSV-1 (KOS strain), HSV-2 (UW-268 strain), vaccinia viruses (D1E strain) or influenza viruses (A/PR/8 strain) and the compounds to be tested were added to monolayers of cells grown on 97-holed culture plates. After incubation, the cytopathic effect (CPE) of the viruses as well as the effect of the compounds on CPE inhibition and on their cytotoxicity were microscopically observed. To estimate the antiviral action of the compounds, TCID$_{50}$ values were found using the CPE as an index and ΔTCID$_{50}$ (log$_{10}$) values were calculated by the TCID$_{50}$ values of both the compound-treated group and the control group. MDCK cells were infected with influenza viruses and Vero cells with other viruses. Bear in mind that prior to be added to the incubation system, the compounds were regulated with MEM media to 10 mg/ml concentrations and diluted with MEM medium with 1% bovin fetus serum.

TABLE 3

Antiviral Spectrum

| Viruses under Test | Antiviral Activity (ΔTCID$_{50}$ (log$_{50}$)) | | |
|---|---|---|---|
| Comp. Concn. (μg/ml) | 1 | 5 | 25 |
| Comp. Ex. 25 | | | |
| Herpes Simplex Viruses | | | |
| Type 1 | 2.04 (−) | >3.19 (−) | >3.31 (±) |
| Type 2 | 1.85 (−) | 2.92 (−) | >3.30 (±) |
| Vaccinia Viruses | 1.70 (−) | 2.67 (−) | 2.53 (±) |
| Influenza Viruses | 1.31 (−) | 1.86 (−) | 2.22 (±) |
| Comp. Ex. 37 | | | |
| Herpes Simplex Viruses | | | |
| Type 1 | 2.74 (−) | 2.65 (−) | >3.25 (−) |
| Type 2 | 1.87 (−) | 3.01 (−) | >3.85 (−) |

TABLE 3-continued

| Viruses under Test | Antiviral Spectrum | | |
|---|---|---|---|
| | Antiviral Activity ($\Delta TCID_{50}$ ($\log_{50}$)) | | |
| Comp. Concn. (μg/ml) | 1 | 5 | 25 |
| Vaccinia Viruses | 1.49 (−) | 2.85 (−) | 2.61 (−) |
| Influenza Viruses | 1.64 (−) | 1.70 (−) | 2.38 (±) |

( ) denotes the magnitude of cytotoxicity [(−): no cytotoxicity, and (±): less cytotoxicity].

Acute Toxicity Testing

The compounds to be tested in the form of a 2% aqueous solution of Tween 80 were orally administered to ICR male mice (weights: 24–30 g), five for each group. Over seven days after the administration of the compounds, they were observed in terms of in what conditions they were and measured in terms of weight. Table 4 shows the results of the $LD_{50}$ values found by the Litchfield-Willcoxon method.

TABLE 4

| Compounds | $LD_{50}$ (mg/kg) |
|---|---|
| Comp. Ex. | |
| 25 | >1000 |
| 37 | >1000 |

In Vivo Antiviral Action

BALB/c male mice of three weeks old, 10 for each group, were abdominally seeded with an infectious amount, $10LD_{50}$, of HSV-1(Miyama strain). One hour later and over six days after the next day, once a day, Compound (5) referred to in Table 1 was continuously administered to each animal via an abdominal route. The results are set out in Table 5.

TABLE 5

| Effect of Compound (5) on the Prolongation of Life of Mice Infected with HSV-1 | |
|---|---|
| Dose (mg/Kg) | Mean Survival Days (average ± standard error) |
| Control | 6.1 ± 0.6 |
| Table 1, Comp. | |
| (5) | 7.9 ± 1.1 |
| (10) | 8.6 ± 0.7* |
| (20) | 11.2 ± 1.1*** | t-Test
*$p < 0.05$, and
***$p < 0.001$

In Vitro Antiviral Action Against Influenza Virus

For incubation, the compounds to be tested and influenza viruses (A/PR/8 strain) were added to monolayers of MDCK cells (epthelial cells derived from a canine kidney) grown. After incubation, the cytopathic effect (CPE) of the viruses as well as the effect of the compounds on CPE inhibition and on their cytotoxicity were microscopically observed. To assay the antiviral action of the compounds, $TCID_{50}$ values were found using the CPE as an index and $\Delta TCID_{50}$ ($\log_{10}$) values were calculated by the $TCID_{50}$ values of both the compound-treated group and the control group. Bear in mind that prior to be added to the incubation systems, the compounds were regulated with ethanol or media to 20 mg/ml concentrations and diluted with media.

TABLE 6

| Antiviral Action of Compounds against Influenza Viruses (A/PR/8 strain) | | | |
|---|---|---|---|
| | Antiviral Activity ($\Delta TCID_{50}$ ($\log_{50}$)) | | |
| Comp. Concn. (μg/ml) | 1 | 5 | 20 |
| Table 1, Comp. | | | |
| (5) | 0.8 (−) | 1.2 (−) | 2.1 (−) |
| (9) | 0.5 (−) | 1.0 (−) | 1.3 (±) |
| (13) | 0.4 (−) | 0.6 (−) | 1.5 (±) |
| Ribavirin | 0.8 (−) | 1.8 (−) | 3.2 (−) |

Investigation was made with MDCK cells. ( ) stands for the magnitude of cytotoxicity [(−): no cytotoxicity, and (±) less cytotoxicity].

Example I of Formulation (Capsule)

A capsule was conventionally prepared according to the following recipe.

| Compound Ex. 25 | 250 mg |
|---|---|
| Magnesium stearate | 5 mg |
| Lactose | suitable amount |
| Total: | 300 mg |

Example II of Formulation (Tablet)

A tablet was conventionally prepared with a suitable vehicle according to the following recipe.

| Compound Ex. 37 | 250 mg |
|---|---|
| Sodium lauryl sulfate | 10 mg |
| Magnesium stearate | 5 mg |
| Polyvinyl pyrrolidone K30 | 11 mg |
| Carboxymethylcellulose (Ca) | 7 mg |
| Lactose | 60 mg |
| Corn starch | suitable amount |
| Total: | 360 mg |

Example III of Formulation (Ointment)

Ointment conventionally prepared according to the following recipe was packed in an aluminium tube.

| Compound Ex. 25 | 3 g |
|---|---|
| White vaseline | suitable amount |

Example IV of Formulation (Hydrogel)

A hydrogel preparation conventionally made according to the following recipe was packed in an aluminium tube.

| Compound Ex. 37 | 3.0 g |
|---|---|
| Hydroxypropylmethylcellulose | 0.1 g |
| Polysorbate 60 | 0.1 g |
| Gelatin | 0.5 g |
| 70% Sorbitol solution | 2.0 g |
| Citric acid | 0.1 g |
| Disodium hydrogen phosphate | 0.3 g |
| Sodium chloride | 0.5 g |
| Benzalkonium chloride | 0.02 g |
| Purified water | suitable amount |
| Total: | 100 g |

Example V of Formulation (Oral Ointment)

Ointment conventionally made according to the following recipe was packed in an aluminium tube.

| | |
|---|---|
| Compound Ex. 25 | 0.3 g |
| Carboxymethylcellulose (Ca) | 3.1 g |
| Liquid paraffin | 3.1 g |
| White vaseline | 1.2 g |
| Plastic base | suitable amount |
| Total: | 10 g |

Example VI of Formulation (Suppository)

| | |
|---|---|
| Compound Ex. 25 | 250 mg |
| Tannic acid | 30 mg |
| Ichthammol | 300 mg |
| Cacao butter | suitable amount |
| Total: | 1000 mg |

Example VI of Formulation (Eye Ointment)

Eye ointment conventionally made according to the following recipe was packed in an aluminium tube.

| | |
|---|---|
| Compound Ex. 37 | 0.3 g |
| Liquid paraffin | 1.0 g |
| White vaseline | suitable amount |
| Total: | 10.0 g |

The novel glycyrrhetinic acid derivatives according to this invention have an improved antirival action and so show excellent effects on the treatment of herpes simplex virus, vaccinia virus and influenza virus. In addition, these compounds are quite different in chemical structure from antiviral agents chiefly made up of a nucleic acid type compounds and now clinically used in the art, so that they can be efficacious against infections due to viruses resistant to these antiviral drugs.

What is claimed is:

1. A glycyrrhetinic acid compound of the formula

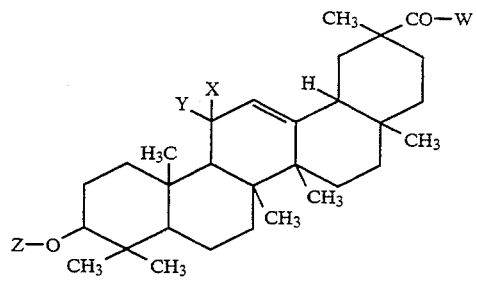

wherein:
X and Y are a hydrogen atom or taken together form an oxo group;
Z is a monosaccharide or disaccharide; and
W is $OR_1$, $NHR_1$ or $R_1$, where $R_1$ is a group of the formula

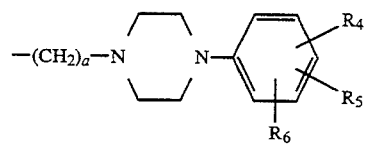

where a is 2; and $R_4$, $R_5$ and $R_6$ are each hydrogen, a halogen or an amino, alkylamino, acylamino, hydroxy, alkyloxy, carboxy, formyl, alkylcarbonyl, alkoxycarbonyl, aryloxycarbonyl, carbamoyl, nitro, cyano, thiol, alkylthio, or a phenyl group;
or a pharmaceutically acceptable salt thereof.

2. 3β-(β-D-glucopyranosyloxy)-N-(2-(4-(2-methoxyphenyl)piperazine-1-yl)ethyl)-18β-olean-12-en-30-amide or a pharmaceutically acceptable salt thereof.

3. 3β-(β-D-glucopyranosyloxy)-N-(2-(4-(2-methoxyphenyl)piperazine-1-yl)ethyl)-11-oxo-18β-olean-12-en-30-amide or a pharmaceutically acceptable salt thereof.

4. 3β-(β-D-glucopyranosyloxy)-N-(2-(4-(2-chlorophenyl)piperazine-1-yl)ethyl)-18β-olean-12-en-30-amide or a pharmaceutically acceptable salt thereof.

5. 3β-(β-D-glucopyranosyloxy)-N-(2-(4-(2-chlorophenyl)piperazine-1-yl)ethyl)-11-oxo-18β-olean-12-en-30-amide or a pharmaceutically acceptable salt thereof.

6. An composition containing a glycyrrhetinic acid derivative or a pharmaceutically acceptable salt thereof as claimed in claim 1 together with a pharmaceutically acceptable carrier.

7. An composition as claimed in claim 6 which further contains a polyoxyethylene higher alcohol ether.

* * * * *